United States Patent
Blann et al.

(10) Patent No.: US 7,323,524 B2
(45) Date of Patent: Jan. 29, 2008

(54) TANDEM TETRAMERISATION-POLYMERISATION OF OLEFINS

(75) Inventors: Kevin Blann, Alberton (ZA); Deon De Wet-Roos, Meyerton (ZA); John Thomas Dixon, Vanderbijlpark (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 0 days.

(21) Appl. No.: 10/538,088

(22) PCT Filed: Dec. 19, 2003

(86) PCT No.: PCT/ZA03/00188

§ 371 (c)(1),
(2), (4) Date: Dec. 2, 2005

(87) PCT Pub. No.: WO2004/056480

PCT Pub. Date: Jul. 8, 2004

(65) Prior Publication Data

US 2006/0128910 A1    Jun. 15, 2006

Related U.S. Application Data

(60) Provisional application No. 60/435,405, filed on Dec. 20, 2002, provisional application No. 60/478,379, filed on Jun. 13, 2003, provisional application No. 60/509,309, filed on Oct. 6, 2003, provisional application No. 60/509,021, filed on Oct. 6, 2003.

(30) Foreign Application Priority Data

| Dec. 20, 2002 | (ZA) | 2002/10339 |
| Jun. 13, 2003 | (ZA) | 2003/4632 |
| Oct. 6, 2003 | (ZA) | 2002/7773 |
| Oct. 6, 2003 | (ZA) | 2003/7774 |

(51) Int. Cl.
C08F 4/609 (2006.01)
C08F 4/6369 (2006.01)
C08F 4/74 (2006.01)
C07C 2/08 (2006.01)
C07C 2/32 (2006.01)

(52) U.S. Cl. .......... 526/116; 526/113; 526/114; 526/348.2; 526/160; 585/510; 585/514; 585/515; 585/520; 585/527

(58) Field of Classification Search ........ 526/113, 526/114, 116, 160, 348.2; 585/511, 514, 585/510, 515, 520, 527, 115
See application file for complete search history.

(56) References Cited

U.S. PATENT DOCUMENTS

| 3,635,937 | A | 1/1972 | Bauer et al. |
| 3,676,523 | A | 7/1972 | Mason |
| 3,906,053 | A | 9/1975 | Lanier |
| 5,331,070 | A | 7/1994 | Pettijohn et al. |
| 5,856,610 | A | 1/1999 | Tamura et al. |
| 6,184,428 | B1 | 2/2001 | Zahoor et al. |
| 6,555,541 | B1 | 4/2003 | Furber et al. |
| 6,586,541 | B2 | 7/2003 | Citron |
| 6,586,550 | B2 | 7/2003 | Cotts et al. |

FOREIGN PATENT DOCUMENTS

| JP | 07215896 A * | 8/1995 |
| WO | WO 01/10876 A1 | 2/2001 |
| WO | WO 02/04119 A1 | 1/2002 |

OTHER PUBLICATIONS

Carter et al., "High Activity Ethylene Trimerisation Catalysts Based on Diphosphine Ligands", Chemical Communication, vol. 2002, No. 8, pp. 858-859, (2002).

* cited by examiner

Primary Examiner—Caixia Lu
(74) Attorney, Agent, or Firm—Finnegan, Henderson, Farabow, Garrett, & Dunner L.L.P.

(57) ABSTRACT

The invention provides a process for polymerising olefins to branched polyolefins in the presence of a polymerisation catalyst and a cocatalyst, wherein the cocatalyst produces 1-octene in a selectivity greater than 30%.

45 Claims, No Drawings

TANDEM TETRAMERISATION-POLYMERISATION OF OLEFINS

CROSS REFERENCE TO RELATED APPLICATIONS

This application is a national phase application based on PCT/ZA2003/000188, filed Dec. 19, 2003, and claims the priority of South African Patent Application Nos. 2002/10339, filed Dec. 20, 2002; 2003/4632, filed Jun. 13, 2003; 2003/7774 filed Oct. 6, 2003; and 2003/7773, filed Oct. 6, 2003; and the benefit of U.S. Provisional Application Nos. 60/435,405, filed on Dec. 20, 2002; 60/478,379, filed on Jun. 13, 2003; 60/509,309, filed on Oct. 6, 2003; and 60/509,021, filed on Oct. 6, 2003, the content of all of which is incorporated herein by reference.

FIELD OF THE INVENTION

This invention relates to a tandem tetramerisation and polymerisation catalyst system and a process for the production of branched polyolefins wherein the polymerisation catalyst can be homogeneous or supported on a support medium.

BACKGROUND TO THE INVENTION

This invention relates to catalyst systems that facilitate the selective production of 1-octene in combination with a suitable polymerisation catalyst so that the in situ polymerisation of the formed 1-octene with the available ethylene feedstock takes place. Preferably, ethylene tetramerisation and polymerisation take place at the same time under the same reaction conditions.

With regard to the oligomerisation catalysts used in this application that are used for the production of 1-octene, the art does not teach a commercially successful process for the tetramerisation of ethylene to produce 1-octene selectively. Conventional ethylene oligomerisation technologies produce a range of α-olefins following either a Schulz-Flory or Poisson product distribution. By definition, these mathematical distributions limit the mass % of the tetramer that can be formed and make a distribution of products. In this regard, it is known from prior art (U.S. Pat. No. 6,184,428) that a nickel catalyst comprising a chelating ligand, preferably 2-diphenyl phosphino benzoic acid (DPPBA), a nickel compound, preferably $NiCl_2.6H_2O$, and a catalyst activator, preferably sodium tetraphenylborate, catalyse the oligomerisation of ethylene to yield a mixture of linear olefins containing 1-octene. The selectivity towards linear $C_8$ α-olefins is claimed to be 19%. Similarly the Shell Higher Olefins Process (SHOP process, U.S. Pat. Nos. 3,676,523 and 3,635,937) using a similar catalyst system is reported to typically yield 11 mass % 1-octene in its product mixture (Chem Systems PERP reports 90-1, 93-6 and 94/95S12).

Ziegler-type technologies based on trialkylaluminium catalysts, independently developed by Gulf Oil Chemicals Company (Chevron, e.g. DE patent 1,443,927) and Ethyl Corporation (BP/Amoco, e.g. U.S. Pat. No. 3,906,053), are also commercially used to oligomerise ethylene to produce mixtures of olefins that reportedly contain 13-25 mass % 1-octene (Chem Systems PERP reports 90-1, 93-6, and 94/95S12).

The prior art also teaches that chromium-based catalysts containing heteroatomic ligands with both phosphorus and nitrogen heteroatoms selectively catalyse the trimerisation of ethylene to 1-hexene. Examples of such heteroatomic ligands for ethylene trimerisation include bis(2-diethylphosphino-ethyl) amine (WO 03/053891) as well as (o-methoxyphenyl)$_2$PN(methyl)P(o-methoxyphenyl)$_2$ (WO 02/04119). Both these catalyst systems and processes are very specific for the production of 1-hexene and only yield 1-octene as an impurity (typically less than 3 mass % of the product mixture as disclosed by WO 02/04119). The coordinating phosphorus heteroatoms in (o-methoxyphenyl)$_2$PN(methyl)P(o-methoxyphenyl)$_2$ (WO 02/04119) are spaced apart by one nitrogen atom. It is believed that the nitrogen atom does not coordinate, at least in the absence of an activator, with the chromium and that without any further electron donating atoms on the ligand that it is a bidentate system. Furthermore it is argued that the polar, or electron donating substituents in the ortho-position of the phenyl groups help form a tridentate system, which is generally believed to enhance selectivity towards 1-hexene formation as reiterated in WO 02/04119 in *Chem. Commun.,* 2002, 858-859: "This has led us to hypothesise that the potential for ortho-methoxy groups to act as pendent donors and increase the coordinative saturation of the chromium centre is an important factor." WO 02/04119 (Example 16) teaches the production of octenes using a trimerisation of olefins process and catalyst system. In this instance, 1-butene was co-trimerised with two ethylene molecules to give 25% octenes. However, the nature of these octenes was not disclosed and the applicant believes that they consist of a mixture of linear and branched octenes.

This application discloses the combination of highly selective tetramerisation cocatalysts for the production of 1-octene and the concomitant polymerisation of the tetramerised olefin with the ethylene feedstock. It has further been found that a chromium-based catalyst containing mixed heteroatomic ligands can be used to selectively tetramerise ethylene to 1-octene often in excess of 60 mass % selectivity. This high 1-octene selectivity cannot be achieved via conventional one-step ethylene oligomerisation technologies which at most yield 25 mass % 1-octene and the present invention confers the suitability of a selective 1-octene yielding catalyst for in situ polymerisation.

Examples of heterogeneous polymerisation processes that mention the polymerisation of in situ formed α-olefins to yield branched by-products of the polymerisation process are known in the art. However, few examples are available describing the combination of a heterogeneous polymerisation catalyst on a support and a homogeneous oligomerisation catalyst, or the combination of two homogeneous catalyst systems where one system produces an α-olefin and the other catalyst polymerises the olefin formed in situ as a comonomer with ethylene. Specific examples related to tandem oligomerisation and polymerisation catalysis involving a supported polymerisation catalyst include U.S. Pat. No. 5,331,070 and EP 0 417 477 in which a metal alkyl, a pyrrole-containing compound and a chromium salt supported on an inorganic support material polymerises an in situ generated α-olefin to yield a branched polyethylene.

Tandem catalysis involving heterogeneous polymerisation catalysts mostly does not involve the combination of a separate oligomerisation catalyst together with a supported polymerisation catalyst as proposed in this application. Due to the nature and geometry of the supported polymerisation catalyst, the formation of α-olefins through β-hydride elimination is possible to some extent, however the formation of polymers is thermodynamically and kinetically more favoured. After an α-olefin is produced it has a high probability to be incorporated into other growing polymer chains as the process of chain growth proceeds from the surface of the support material. In this way, polymers containing relatively low amounts of α-olefins are produced without significant control over the extent of α-olefin incorporation or the resultant polymer architecture.

Although examples of homogeneous tandem catalysis involving the combination of oligomerisation catalysts in tandem with suitable soluble polymerisation catalysts are rare, the recent patent literature such as U.S. Pat. Nos. 6,586,541, 6,555,631 and 6,586,550 specifically relate to the deliberate combination of oligomerisation catalysts, previously reported for their ability to produce α-olefins, combined with soluble polymerisation catalysts to produce branched polyolefins.

These patent examples centre on contacting both an oligomerisation catalyst and a polymerisation catalyst with a single feedstock namely ethylene. Both oligomers and polymers are produced in the same system with concurrent production of α-olefins and the polymerisation of the resultant α-olefins with ethylene. Most of the oligomerisation catalysts that convey novelty to these patents are oligomerisation catalysts that produce a distribution of α-olefins. These distributions are favoured towards a mixture of 1-butene, 1-hexene, 1-octene and 1-decene. Consequently, the structure of the polymers described in these patents exhibit patterns of incorporation according to $^{13}C$ NMR analysis that reflect the distribution of α-olefins.

It is well-known in the open literature that control of reaction conditions such as pressure, temperature, feed gas make-up, comonomer content etc. result in polymers with desirable physical properties such as tear-strength, optical clarity, elasticity and many other physical properties deemed desirable by polymer end-users. In particular, the production of linear low-density polyethylene (LLDPE) sees the polymerisation of individual high purity α-olefins, such as 1-butene, 1-hexene and 1-octene, and ethylene to produce LLDPE suitable for films and sheets, blow molding, extrusion and wire and cable jacket material as well as rotational molding material. In none of the above examples is there disclosed a process relating to the selective production of 1-octene for in situ incorporation into polyethylene.

The combination of the highly selective ethylene tetramerisation catalyst system of the present disclosure with a suitable polymerisation catalyst can therefore result in a tandem process that produces polyethylene grades with high end-user specifications without the need of a separate facility or process to manufacture the 1-octene.

It will be understood that tandem oligomerisation and polymerisation catalysis includes in situ catalysis. In-situ catalysis means oligomerisation and polymerisation catalysis in the same reaction medium. The tandem oligomerisation and polymerisation catalysis may be in situ concurrent and/or in situ consecutive catalysis. The individual components of the oligomerisation and polymerisation catalysts may thus be added together simultaneously or sequentially, in any order, and in the presence or absence of monomer in a suitable solvent. Reaction mixture will be understood to include a reaction medium, reaction products and catalyst components. The reaction medium normally includes a solvent.

SUMMARY OF THE INVENTION

This invention generally relates to the need for selectively producing 1-octene from ethylene and concomitant polymerisation of this monomer with ethylene can be satisfied by using a separate distinct transition metal-based ethylene tetramerisation catalyst system containing a heteroatomic ligand in tandem with a separate distinct polymerisation catalyst comprising a transition metal and hetero or homoatomic ligands.

By homoatomic is meant a ligand that consists entirely of similar atoms such as carbon that constitute the skeleton of the ligand such as the cyclopentadienyl ligand for example.

Thus, according to a first aspect of the invention, there is provided a process for polymerising olefins to produce branched polyolefins in the presence of a polymerisation catalyst and a cocatalyst, wherein the cocatalyst produces 1-octene in a selectivity greater than 30% and the 1-octene produced is at least partially incorporated into the polyolefin chain.

The invention allows the cocatalyst and/or process conditions to be selected to produce more than 40%, 50%, 60% or 70% 1-octene and the said 1-octene is at least partially incorporated into the polyolefin chain.

In this specification, % will be understood to be a mass %.

The branched polyolefin may be a branched polyethylene.

The branched polyolefin may be linear low density polyethylene (LLDPE).

The cocatalyst may be an ethylene tetramerisation catalyst, which includes a transition metal precursor and a heteroatomic ligand.

In this specification the term "tetramerisation" refers to a catalytic reaction of a single olefinic monomer or a mixture of olefinic monomers giving products enriched in tetramers derived from those olefinic monomers. The tetramerisation product stream may consist of linear or branched olefins.

By heteroatomic tetramerisation ligand is meant a ligand that contains at least two heteroatoms, which can be the same or different, where the heteroatoms may be selected from phosphorus, arsenic, antimony, sulphur, oxygen, bismuth, selenium or nitrogen.

The heteroatomic ligand for the ethylene tetramerisation catalyst may be described by the following general formula $(R)_nA$-$B$-$C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group and n and m are determined by the respective valence and oxidation state of A and C.

A and/or C may be a potential electron donor for coordination with the transition metal.

An electron donor is defined as that entity that donates electrons used in chemical, including dative covalent, bond formation.

The heteroatomic ligand for the ethylene tetramerisation catalyst may be described by the following general formula $(R^1)(R^2)A$-$B$-$C(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently selected from hydrocarbyl or heterohydrocarbyl or substituted hydrocarbyl or substituted heterohydrocarbyl groups.

The heteroatomic ligand for the ethylene tetramerisation catalyst may be described by the following general formula $(R^1)(R^2)A$-$B$-$C(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently non-aromatic or aromatic, including heteroaromatc, groups.

$R^1$, $R^2$, $R^3$ and $R^4$ may be aromatic, including heteroaromatic, groups and preferably not all the groups $R^1$, $R^2$, $R^3$ and $R^4$, if aromatic, have a substituent on the atom adjacent to the atom bound to A or C.

$R^1$, $R^2$, $R^3$ and $R^4$ may have substituents on the atom adjacent to the atom bound to A or C.

At least one or more of $R^1$, $R^2$, $R^3$ and $R^4$ may be substituted with a polar substituent on a second or further atom from the atom bound to A or C.

Any polar substituents on $R^1$, $R^2$, $R^3$ and $R^4$ may preferably not be on the atom adjacent to the atom bound to A or C.

Any polar substituent on one or more of $R^1$, $R^2$, $R^3$ and $R^4$ may be electron-donating.

Any substituents on one or more of $R^1$, $R^2$, $R^3$ and $R^4$ may be not electron-donating.

In another embodiment, each non-electron donating substituent may be non-polar.

Each of $R^1$, $R^2$, $R^3$ and $R^4$ may be aromatic, including heteroaromatic, but not all of $R^1$, $R^2$, $R^3$ and $R^4$ are substituted by any substituent on an atom adjacent to the atom bound to A or C.

Preferably, not more than two of $R^1$, $R^2$, $R^3$ and $R^4$ may have substituents on the atom adjacent to the atom bound to A or C.

Polar is defined by IUPAC as an entity with a permanent electric dipole moment. Polar substituents include methoxy, ethoxy, isopropoxy, $C_3$-$C_{20}$ alkoxy, phenoxy, pentafluorophenoxy, trimethylsiloxy, dimethylamino, methylsulfanyl, tosyl, methoxymethy, methylthiomethyl, 1,3-oxazolyl, methoxymethoxy, hydroxyl, amino, phosphino, arsino, stibino, sulphate, nitro and the like.

Any of the groups in the ligand for the tetramerisation catalyst, $R^1$, $R^2$, $R^3$ and $R^4$ may independently be linked to one or more of each other or to the linking group B to form a cyclic structure together with A and C, A and B or B and C.

$R^1$, $R^2$, $R^3$ and $R^4$ in the tetramerisation ligand may be independently selected from a group comprising a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group. Preferably, $R^1$, $R^2$, $R^3$ and $R^4$ may independently be selected from a group comprising a phenyl, tolyl, biphenyl, naphthyl, thiophenyl and ethyl group.

B may be selected from any one of a group comprising: organic linking groups comprising a hydrocarbylene, a substituted hydrocarbylene, a heterohydrocarbylene and a substituted heterohydrocarbylene; inorganic linking groups comprising single atom links; ionic links and a group comprising methylene, dimethylmethylene, 1,2-ethylene, 1,2-phenylene, 1,2-propylene, 1,2-catecholate, —($CH_3$)N— N($CH_3$)—, —B($R^5$)—, —Si($R^5$)$_2$—, —P($R^5$)—, and —N($R^5$)—, where $R^5$ is hydrogen, a hydrocarbyl or substituted hydrocarbyl, a substituted heteroatom or a halogen. Preferably, B may be —N($R^5$)— and $R^5$ is a hydrocarbyl or a substituted hydrocarbyl group. $R^5$ may be hydrogen or may be selected from the groups consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^5$ may be an isopropyl, a 1-cyclohexylethyl, a 2-methylcyclohexyl or a 2-octyl group.

In another embodiment of the invention any of the groups in the ligand for the tetramerisation catalyst, $R^1$, $R^2$, $R^3$, $R^4$ or $R^5$ may include any cyclic heteroatomic group such as a cyclopentadienyl-dimethylsilyl-t-butyl group or a cyclic homoatomic group such as a cyclopentadienyl, indenyl or fluorene group.

B may be selected to be a single atom spacer. A single atom linking spacer is defined as a substituted or non-substituted atom that is bound directly to A and C.

A and/or C may be independently oxidised by S, Se, N or O.

A and C may be independently phosphorus or phosphorus oxidised by S or Se or N or O.

The tetramerisation ligand may also contain multiple (R)$_n$A-B-C(R)$_m$ units. Not limiting examples of such ligands include dendrimeric ligands as well as ligands where the individual units are coupled either via one or more of the R groups or via the linking group B. More specific, but not limiting, examples of such ligands may include 1,2-di-(N(P (phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P (phenyl)$_2$)-benzene, 1,2-di-N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-P(p-methoxyphenyl)N(methyl)P(p-methoxyphenyl)$_2$)-benzene.

The heteroatomic ligands for tetramerisation can be prepared using procedures known to one skilled in the art and procedures disclosed in published literature. Examples of ligands are: (phenyl)$_2$PN(methyl)P(phenyl)$_2$, (phenyl)$_2$PN (pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-$^t$butylphenyl)P(phenyl)$_2$, (phenyl)$_2$PN((CH$_2$)$_3$-N-morpholine)P (phenyl)$_2$, (phenyl)$_2$PN(Si(CH$_3$)$_3$)P(phenyl)$_2$, (((phenyl)$_2$ P)$_2$ NCH$_2$CH$_2$)N, (ethyl)$_2$PN(methyl)P(ethyl)$_2$, (ethyl)$_2$PN (isopropyl)P(phenyl)$_2$, (ethyl)(phenyl)PN(methyl)P(ethyl) (phenyl), (ethyl)(phenyl)PN(isopropyl)P(phenyl)$_2$, (phenyl)$_2$ P(=Se)N(isopropyl)P(phenyl)$_2$, (phenyl)$_2$PCH$_2$CH$_2$P (phenyl)$_2$, (oethylphenyl)(phenyl)PN(isopropyl)P(phenyl)$_2$, (o-methylphenyl)$_2$PN(isopropyl)P(omethylphenyl)(phenyl), (phenyl)$_2$PN(benzyl)P(phenyl)$_2$, (phenyl)$_2$PN(1-cyclohexylethyl)P(phenyl)$_2$, (phenyl)$_2$PN[CH$_2$CH$_2$CH$_2$Si(OMe$_3$)]P (phenyl)$_2$, (phenyl)$_2$PN(cyclohexyl)P(phenyl)$_2$, phenyl)$_2$PN (2-methylcyclohexyl)P(phenyl)$_2$, (phenyl)$_2$PN(allyl)P (phenyl)$_2$, (2-naphthyl)$_2$PN(methyl)P(2-naphthyl)$_2$, (p-biphenyl)$_2$PN(methyl)P(p-biphenyl)$_2$, (p-methylphenyl)$_2$ PN(methyl)P(p-methylphenyl)$_2$, (2-thiophenyl)$_2$PN(methyl) P(2-thiophenyl)$_2$, (phenyl)$_2$PN(methyl)N(methyl)P (phenyl)$_2$, (m-methylphenyl)$_2$PN(methyl)P(m-methylphenyl)$_2$, (phenyl)$_2$PN(isopropyl)P(phenyl)$_2$ and (phenyl)$_2$P (=S)N(isopropyl)P(phenyl)$_2$.

Examples of ligands with polar substituents on $R^1$, $R^2$, $R^3$ and $R^4$ include: (m-methoxyphenyl)$_2$PN(methyl)P(m-methoxyphenyl)$_2$, (p-methoxyphenyl)$_2$PN(methyl)P(p-methoxyphenyl)$_2$, (m-methoxyphenyl)$_2$PN(isopropyl)P(m-methoxyphenyl)$_2$, (p-methoxyphenyl)$_2$PN(isopropyl)P(p-methoxyphenyl), (p-methoxyphenyl)$_2$PN(2-ethylhexyl)P(p-methoxyphenyl)$_2$, (m-methoxyphenyl)(phenyl)PN(methyl) P(phenyl)$_2$ and (p-methoxyphenyl)(phenyl)PN(methyl)P (phenyl)$_2$, (m-methoxyphenyl) (phenyl)PN(methyl)P(m-methoxyphenyl)(phenyl), (p-methoxyphenyl) (phenyl)PN (methyl)P(p-methoxyphenyl)(phenyl), (m-methoxyphenyl)$_2$ PN(methyl)P(phenyl)$_2$ and (p-methoxyphenyl)$_2$PN(methyl) P(phenyl)$_2$, (p-methoxyphenyl)$_2$PN(1-cyclohexylethyl)P(p-methoxyphenyl)$_2$, (p-methoxyphenyl)$_2$PN(2-methylcyclohexyl)P(p-methoxyphenyl)$_2$, (p-methoxyphenyl)$_2$PN(decyl) P(p-methoxyphenyl), (p-methoxyphenyl)$_2$PN(pentyl)P(p-methoxyphenyl)$_2$, (p-methoxyphenyl)₂PN(benzyl)P(p-methoxyphenyl)₂, (p-methoxyphenyl)₂PN(phenyl)P(p-methoxyphenyl)₂, (p-fluorophenyl)₂PN(methyl)P(p-fluorophenyl)₂, (o-fluorophenyl)₂PN(methyl)P(o-fluorophenyl)₂, (p-dimethylamino-phenyl)₂PN(methyl)P(p-dimethylamino-phenyl)₂, (p-methoxyphenyl)₂PN(allyl)P(p-methoxyphenyl)₂, (phenyl)₂PN(isopropyl)P(o-methoxyphenyl)₂, (p-(p-methoxyphenyl)-phenyl)PN(isopropyl)P(p-(p-methoxyphenyl)phenyl)₂ and (p-methoxyphenyl)(phenyl)PN(isopropyl)P(phenyl)₂.

The heteroatomic tetramerisation ligand can be modified to be attached to a polymer chain so that the resulting heteroatomic coordination complex of the transition metal is soluble at elevated temperatures, but becomes insoluble at 25° C. This approach would enable the recovery of the complex from the reaction mixture for reuse and has been used for other catalyst as described by D. E. Bergbreiter et al., *J. Am. Chem. Soc.*, 1987, 109, 177-179. In a similar vein these transition metal complexes can also be immobilised by binding the heteroatomic ligands to silica, silica gel, polysiloxane or alumina backbone as, for example, demonstrated by C. Yuanyin et al., *Chinese J. React. Pol.*, 1992, 1(2), 152-159 for immobilising platinum complexes.

With regard to the tetramerisation process, the process may include the step of generating a heteroatomic tetramerisation coordination complex from a transition metal precursor and a heteroatomic ligand and adding a polymerisation catalyst either at the same time or over a period of time. The process may include the step of adding a pre-formed coordination complex, prepared using a heteroatomic ligand and a transition metal precursor, to a reaction mixture, or the step of adding separately to the reactor, a heteroatomic ligand and a transition metal precursor such that a heteroatomic coordination complex of a transition metal is generated in situ. In all cases, the polymerisation catalyst may be added to the reactor at the same time as the tetramerisation catalyst or the polymerisation catalyst may be fed sequentially into the reactor over a period of time. By generating a heteroatomic coordination complex in situ is meant that the complex is generated in the medium in which catalysis takes place. Typically, the heteroatomic coordination complex is generated in situ. Typically, the transition metal precursor, and heteroatomic ligand are combined (both in situ and ex situ) to provide metal/ligand ratios from about 0.01:100 to 10 000:1, and preferably, from about 0.1:1 to 10:1.

The tetramerisation cocatalyst, as defined previously to include a transition metal precursor and a heteroatomic ligand, can be combined with the polymerisation catalyst in the ratio 0.01:100 to 10 000:1, and preferably, from about 1:1 to 100:1.

With regard to the tetramerisation transition metal precursor, the transition metal may be selected from any one of a group comprising chromium, molybdenum, tungsten, titanium, tantalum, vanadium and zirconium, preferably chromium.

With regard to the tetramerisation catalyst, the transition metal precursor which, upon mixing with the heteroatomic ligand and an activator, catalyses ethylene tetramerisation in accordance with the invention, may be a simple inorganic or organic salt, a coordination or organometallic complex and may be selected from any one of a group comprising chromium trichloride tris-tetrahydrofuran complex, (benzene)-tricarbonyl chromium, chromium (III) octanoate, chromium hexacarbonyl, chromium (III) acetylacetonate and chromium (III) 2-ethylhexanoate. The preferred transition metal precursors include chromium (III) acetylacetonate and chromium (III) 2-ethylhexanoate.

The process may include the step of combining in any order a heteroatomic ligand with a transition metal precursor, a polymerisation catalyst and an activator.

Examples of suitable polymerisation catalysts for the polymerisation of ethylene and the in situ synthesised 1-octene include but are not limited to the following:

Ziegler-Natta Catalysts

TiCl₃-Et₂AlCl, AlR₃—TiCl₄, wherein R belongs to the group comprising of alkyl, substituted alkyl, cyclic alkyl, aryl, substituted aryl, alkene and substituted alkene, and the like.

Unbridged Metallacenes Bis(cyclopentadienyl)-chromium (II), bis(cyclopentadienyl)-zirconium chloride hydride, bis (cyclopentadienyl)-ytitanium dichloride, bis(cyclopentadienyl)-zirconium dichloride, bis(cyclopentadienyl)-zirconium dimethyl, bis(n-butylcyclopentadienyl)-zirconium dichloride, bis(n-dodecylcyclopentadienyl)-zirconium dichloride, bis(ethylcyclopentadienyl)-zirconium dichloride, bis(iso-butylcyclopentadienyl)-zirconium dichloride, bis(isopropylcyclopentadienyl)-zirconium dichloride, bis(methylcyclopentadienyl)-zirconium dichloride, bis(n-octylcyclopentadienyl)-zirconium dichloride, bis (n-pentylcyclopentadienyl)-zirconium dichloride, bis(n-propylcyclopentadienyl)-zirconium dichloride, bis (trimethylsilylcyclopentadienyl)-zirconium dichloride, bis (1,3-bis(trimethylsilyl)cyclopentadienyl)-zirconium dichloride, bis(1-ethyl-3-methylcyclopentadienyl)-zirconium dichloride, bis(pentamethylcyclopentadienyl)-zirconium dichloride, bis(pentamethylcyclopentadienyl)-zirconium dimethyl, bis(1-propyl-3-methylcyclopentadienyl)-zirconium dichloride, bis(4,7-dimethylindenyl)-zirconium dichloride, bis(indenyl)-zirconium dichloride, bis(2-methylindenyl)-zirconium dichloride, bis(2-methylindenyl)-zirconium dichloride, cyclopentadienylindenyl-zirconium dichloride Half Sandwich Metallocenes Cyclopentadienyl-zirconium trichloride, pentamethylcyclopentadienyl titanium trichloride, pentamethylcyclopentadienyl-titanium trimethoxide, trimethyl-titanium-pentamethylcyclopentadienide, pentamethylcyclopentadienyl-zirconium trichloride, tetramethylcyclopentadienyl-zirconium trichloride, 1,2,4-trimethylcyclopentadienyl-zirconium trichloride Carbon-Bridged Metallocenes Diphenylmethylidene(cyclopentadienyl)-(9-fluorenyl)-zirconium dichloride, diphenylmethylidene(cyclopentadienyl)-(indenyl)-zirconium dichloride, isopropylidene-bis (cyclopentadienyl)-zirconium dichloride, isopropylidene-(cyclopentadienyl)(9-fluorenyl)-zirconium dichloride, isopropylidene-(3-methylcyclopentadienyl)-(9-fluorenyl)-zirconium dichloride, ethylene-bis(9-fluorenyl)-zirconium dichloride, mesethylene-bis(1-indenyl)-zirconium dichloride, rac-ethylene-bis(1-indenyl)-zirconium dichloride, rac-ethylene-bis(1-indenyl)-zirconium dimethyl, rac-ethylene-bis(2-methyl-1-indenyl)-zirconium dichloride, rac-ethylene-bis(4,5,6,7-tetrahydro-1-indenyl)-zirconium dichloride Silyl-Bridged Metallocenes Dimethylsilyl-bis(cyclopentadienyl)-zirconium dichloride, dimethylsilyl-bis(9-fluorenyl)-zirconium dichloride, rac-dimethylsilyl-bis(1-indenyl)-zirconium dichloride, meso-dimethylsilyl-bis(2-methylindenyl)-zirconium dichloride, rac-dimethylsilyl-bis(2-methylindenyl)-zirconium dichloride, rac-dimethylsilyl-bis(tetrahydroindenyl)-zirconium dichloride, dimethylsilyl-bis(tetramethylcyclopentadienyl)-zirconium dichloride, diphenylsilyl(cyclopentadienyl) (9-fluorenyl)-zirconium dichloride, diphenylsilyl-bis (indenyl)hafnium dichloride.

The activator for use in the process may in principle be any compound that generates an active catalyst when combined with the heteroatomic ligand and the transition metal precursor. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

Suitable organoaluminium compounds include compounds of the formula $AlR_3$, where each R is independently a $C_1$-$C_{12}$ alkyl, an oxygen containing moiety or a halide, and compounds such as $LiAlH_4$ and the like. Examples include trimethylaluminium (TMA), triethylaluminium (TEA), triisobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes. Aluminoxanes are well known in the art as oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

Examples of suitable organoboron compounds are boroxines, $NaBH_4$, triethylborane, tris(pentafluorophenyl)borane, tributyl borate and the like.

The activator may also be or contain a compound that acts as a reducing or oxidising agent, such as sodium or zinc metal and the like, or oxygen and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups.

The transition metal precursor of the tetramerisation catalyst and the aluminoxane may be combined in proportions to provide Al/metal ratios from about 1:1 to 10 000:1, preferably from about 1:1 to 1000:1, and more preferably from 1:1 to 300:1.

The process may include the step of adding to the catalyst system (including both the polymerisation and olefin tetramerisation catalysts) a trialkylaluminium compound in amounts of between 0.01 to 1000 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The activator may also be a binuclear cocatalyst such as a bisborane 1,4-$(C_6F_5)_2B(C_6F_4)B$-$(C_6F_5)_2$. This binuclear cocatalyst may be combined with the tetramerisation and polymerisation catalysts in such a way that a bimolecular species may be formed that has metal centres in close molecular proximity.

The catalyst systems or its individual components, in accordance with the invention, or its individual components, may also be immobilised by supporting it on a support material, for example, silica, alumina, $MgCl_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the polymerisation catalyst. In some cases, the support material can also act as a component of the activator. This approach would also facilitate the recovery of the catalyst from the reaction mixture for reuse. The concept was, for example, successfully demonstrated with a chromium-based ethylene trimerisation catalyst by T. Monoi and Y. Sasaki, *J. Mol. Cat.A: Chem.*, 1987, 109, 177-179. In some cases, the support can also act as a catalyst component, for example where such supports contain aluminoxane functionalities or where the support is capable of performing similar chemical functions as an aluminoxane, which is for instance the case with IOLA™ (a commercial product from Grace Davison).

According to a further aspect of the invention, there is provided a tandem oligomerisation and polymerisation process for the oligomerisation of ethylene to produce an olefinic product stream and the in situ polymerisation of the oligomeric olefin with ethylene, the process including the step of contacting the olefins with an oligomerisation catalyst, which catalyst includes a heteroatomic ligand and a transition metal precursor, and a polymerisation catalyst, which catalyst includes a transition metal and and/or a homo- or heteroatomic ligand.

The oligomerisation catalyst may be an ethylene tetramerisation catalyst.

According to yet another aspect of the Invention the tetramerisation process includes the step of contacting an olefinic feedstream with a catalyst system which includes a transition metal and a heteroatomic ligand and wherein the product of the tetramerisation process is an olefin and the olefin is concomitantly copolymerised with the olefinic feedstream by contacting the olefins produced in the first step and the olefinic feedstream with a catalyst comprising of a transition metal and/or a homo- or heteroatomic ligand.

By homoatomic is meant a ligand that consists entirely of similar atoms such as carbon that constitute the skeleton of the ligand such as the cyclopentadienyl ligand for example.

The ethylene to be tetramerised and polymerised can be introduced into the process according to the invention in a continuous or batch fashion.

The tandem catalysis product stream will be understood to include a polymer, which polymer is produced according to the invention in a continuous or batch fashion.

The process may include a process for tetramerisation of ethylene to selectively yield 1-octene.

The process may be a process for tetramersation of ethylene and concomitant polymerisation of the produced 1-octene with ethylene.

The ethylene may be contacted with the catalyst system comprising of the tetramerisation catalyst and the polymerisation catalyst at a pressure of 100 kpa (1 barg), preferably greater than 1000 kpa (10 barg), more preferably greater than 3000 kpa (30 barg).

The tandem catalysis process may include the step of mixing the components of the catalyst systems (both the tetramerisation catalyst and the polymerisation catalyst) at any temperature between −20° C. and 250° C. in the presence of an olefin. The preferred temperature range being 20° C.-100° C.

The individual components of both catalyst systems described herein may be combined simultaneously or sequentially in any order, and in the presence or absence of a solvent, in order to give active catalysts. The presence of an olefin during the mixing of the catalyst components generally provides a protective effect which may result in improved catalyst performance. The preferred temperature range may be between 20° C. and 100° C.

The reaction products derived from the tandem catalysis process as described herein, may be prepared using the disclosed catalyst system by a homogeneous liquid phase reaction in the presence or absence of an inert solvent, and/or by slurry reaction where the catalyst system is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The tandem catalysis process may also be carried out in an inert solvent. Any inert solvent that does not react with the activator can be used. These inert solvents may include, saturated aliphatic, unsaturated aliphatic, aromatic hydrocarbon and halogenated hydrocarbon. Typical solvents include, but are not limited to, benzene, toluene, xylene, cumene, heptane, methylcyclohexane, methylcyclopentane, cyclohexane, ionic liquids and the like.

The tandem catalysis process may be carried out at pressures from atmospheric to 50000 kpa (500 barg). Ethylene pressures in the range of 1000-7000 kpa (10-70 barg) are preferred. Particularly preferred pressures range from 3000-5000 (30-50 barg).

The tandem catalysis process may be carried out at temperatures from −20° C.-250° C. Temperatures in the range of 15-130° C. are preferred. Particularly preferred temperatures range from 35-150° C.

The tandem catalysis process may be carried out in a plant which includes any type of reactor. Examples of such reactors include, but are not limited to, batch reactors, semi-batch reactors and continuous reactors. The plant may include, in combination a) a reactor, b) at least one inlet line into this reactor for olefin reactant and the catalyst system, c) effluent lines from this reactor for polymerisation reaction products, and d) at least one separator to separate the desired polymerisation reaction products, wherein the catalyst system may include a heteroatomic ligand, a transition metal precursor, a polymerisation catalyst and an activator, as described herein.

In another embodiment of this invention, a combination of reactors may be preferred where the first reactor may be a continuously stirred tank reactor and the second reactor may be a batch, continuously stirred tank reactor or a plug-flow reactor.

EXAMPLES OF PERFORMING THE INVENTION

The invention will now be described with reference to the following non-limiting examples. The individual components of the examples may conceivably be omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. All trialkylaluminium and aluminoxane compounds and solutions thereof were obtained from Crompton Gmbh, Akzo Nobel and Albemarle Corporation. In all the examples, the molar mass of methylaluminoxane (MAO) was taken to be 58.016 g/mol, corresponding to the ($CH_3$—Al—O) unit, in order to calculate the molar quantities of MAO used in the preparation of the catalysts described in the examples below. Ethylene oligomerisation products were analysed by GC-MS and GC-FID. Polymer samples were dried under vacuum for 12 hours prior to characterisation. Polymers were characterised using differential scanning calorimetry (DSC) to determine melting points and $^{13}C$ NMR for the determination of the mol % incorporation of α-olefins. Where possible the remaining liquid after tandem polymerisation was analysed by GC-FID for residual olefin composition.

Example 1

Ethylene Tetramerisation Reaction Using $CrCl_3$ ($THF_3$), (p-methoxyphenyl)$_2$PN(isopropyl)P(p-methoxyphenyl)$_2$ and MAO A solution of 9.8 mg of (pmethoxyphenyl)$_2$PN(isopropyl) P(pmethoxyphenyl)$_2$ (0.018 mmol) in 10 ml of toluene was added to a solution of 5.6 mg $CrCl_3(THF)_3$ (0.015 mmol) in 10 ml toluene in a Schilenk vessel. The mixture was stirred for 5 min at ambient temperature and was then transferred to a 300 ml pressure reactor (autoclave) containing a mixture of toluene (80 ml) and MAO (methylaluminoxane, 4.5 mmol) at 40° C. The pressure reactor was charged with ethylene after which the reactor temperature was maintained at 45° C., while the ethylene pressure was kept at 4500 kpa (45 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.0831 g of polyethylene. The GC analyses indicated that the reaction mixture contained 42.72 g oligomers. The oligomers comprised 72% 1-octene (99% purity).

Example 2

Ethylene Tetramerisation Reaction Using Cr(acetylacetonate)$_3$, (phenyl)$_2$PN(isopropyl)P(phenyl)$_2$ and MAO A solution of 18.8 mg of (phenyl)$_2$PN(isopropyl)P(phenyl)$_2$ (0.044 mmol) in 6.4 ml of cumene was added to a solution of 7.7 mg Cr(acetylacetonate)$_3$ (0.022 mmol) in 8 ml cumene in a Schilenk vessel. The mixture was stirred for 5 min at ambient temperature and was then transferred to a 1000 ml pressure reactor (autoclave) containing a mixture of cumene (180 ml) and MAO (methylaluminoxane, 4.4 mmol, 10% solution in toluene) at 40° C. The pressure reactor was charged with ethylene after which the reactor temperature was controlled at 45° C., while the ethylene pressure was maintained at 4500 kpa (45 barg). The reaction was terminated after 25 min, and the procedure of Example 2 above was employed. The product mass was 118.78 g. The product comprised 69.5% 1-octene (98.9% purity).

Example 3

Tandem Catalysis Reaction Using Cr(acetylacetonate)$_3$, (phenyl)$_2$PN(isopropyl)P(phenyl)$_2$, MAO and dimethylsilyl-bis(2-methyl{4,5}benzoindenyl) zirconium dichloride In this example, 0.011 mmol Chromium acetylacetonate (15.2 mg) was combined with 0.022 mmol (phenyl)$_2$PN (isopropyl)P(phenyl)$_2$ (36 mg) in a Schlenk tube under an argon atmosphere with 10 ml anhydrous toluene as solvent. The metal salt and the ligand was stirred for 5 minutes and then added under inert conditions to a Parr autoclave (300 ml capacity). The autoclave was filled a priori with 70 ml anhydrous toluene as solvent. Separately, 2 ml of a solution of dimethylsilyl-bis(2-methyl(4,5)benzoindenyl) zirconium dichloride (0.0052 mmol, 0.0022 mg) was added to 18 ml anhydrous toluene in a separate reservoir under inert conditions connected to the inlet of an HPLC pump. Approximately 1200 eq (on Cr) methylaluminoxane (MAO) was added to the autoclave under argon atmosphere. The autoclave was heated to 45° C., sealed and pressurised to 3500 kpa (35 barg) with ethylene whilst stirring was commenced at 1200 rpm. At the same time the polymerisation catalyst solution was added to the autoclave through an inlet on the Parr reactor that was connected to the outlet of the HPLC pump. The polymerisation catalyst was added at a rate of 0.66 ml/min over a period of 30 minutes after which the reaction vessel was cooled down and quenched with ethanol. After 30 minutes, the autoclave was opened and the contents collected for analysis. The amount of polymer collected was found to be 23.16 g with a melting point of 126° C. and an amount of 1-octene incorporation as determined by $^{13}$C nuclear magnetic resonance spectroscopy of 3.83%.

Example 4

Tandem Catalysis Reaction Using Cr(acetylacetonate)$_3$, (phenyl)$_2$PN(isopropyl)P(phenyl)$_2$, MAO and tetramethylcyclopentadienyl dimethylsilyl t-butylamidato titanium dichloride In this example, a solution of 20 ml (phenyl)$_2$PN(isopropyl)P(phenyl)$_2$ (0.044 mmol) in anhydrous toluene and 20 ml of a solution of Cr(acetylacetonate)$_3$ (0.022 mmol) in 30 ml anhydrous toluene was added to a Parr autoclave (300 ml capacity). At the same time, 10 ml of a solution of tetramethylcyclopentadienyl-dimethylsilyl-t-butylamidato titanium dichloride (0.026 mmol, 0.01 mg ) was added to an external reservoir along with 10 ml anhydrous toluene. The external reservoir (under argon atmosphere) was connected to the inlet of an HPLC pump. Approximately 1200 eq (on Cr) methylaluminoxane (MAO) was added to the autoclave under inert conditions. The autoclave was heated to 45° C., sealed and pressurised to 4300 kpa (43 barg) with ethylene whilst stirring was commenced at 1200 rpm. At the same time the polymerisation catalyst solution was added to the autoclave through a separate inlet on the Parr reactor that was connected to the outlet of the HPLC pump. The polymerisation catalyst was added at a rate of 0.66 ml/min over a period of 30 minutes after which the reaction vessel was cooled down and quenched with ethanol. The autoclave was opened and the contents collected for analysis. Analysis of the polymer after drying in vacuum for 12 h at 60° C. revealed a melting point of 99° C. and 2.39% incorporation of 1-octene as determined using $^{13}$C NMR. The amount of polymer collected was 24.53 g. The density of the polymer was determined to be 0.9202 g.cm$^{-3}$.

Example 5

Tandem Catalysis Reaction Using (p-methoxyphenyl)$_2$PN(isopropyl)P(p-methoxyphenyl)$_2$, Cr(acetylacetonate)$_3$, MAO and dimethylsilyl bisindenyl zirconium dichloride In this example, 10 ml of a toluene solution containing 0.03 mmol chromium acetylacetonate was combined with 0.06 mmol (p-methoxyphenyl)$_2$PN(isopropyl)P(p-methoxyphenyl)$_2$[30 mg] in a Schlenk tube under an argon atmosphere. The metal salt and the ligand was stirred for 5 minutes and then added to a Parr autoclave (300 ml capacity) under inert conditions. The autoclave was filled a priori with 60 ml anhydrous toluene as solvent. Separately, 5 ml of a solution of dimethylsilyl bisindenyl zirconium dichloride (0.015 mmol, 0.0067 mg), was added to 15 ml anhydrous toluene in a separate reservoir under argon that was connected to the inlet of an HPLC pump. Approximately 600 eq (on Cr) methylaluminoxane (MAO) was added to the autoclave under inert conditions. The autoclave was heated to 45° C., sealed and pressurised to a pressure of 4100 kpa (41 barg) with ethylene whilst stirring was commenced at 1200 rpm. At the same time the polymerisation catalyst solution was added to the autoclave through a separate inlet connected to the outlet of the HPLC pump. The polymerisation catalyst was added at a rate of 0.33 ml/min over a period of 60 minutes after which the reaction vessel was cooled down and quenched with ethanol. The autoclave was opened and the contents collected for analysis. The amount of polymer collected was first dried in a vacuum oven at 60° C. for 12 h yielding an amount of 51.1 g with a melting point of 106° C. and an amount of 1-octene incorporated as determined by $^{13}$C nuclear magnetic resonance spectroscopy of 5.55%. The density of the polymer was determined to be 0.8155 g.cm$^{-3}$.

Example 6

Tandem Catalysis Reaction Using (p-methoxyphenyl)$_2$-PN(isopropyl)P(p-methoxyphenyl)$_2$, Cr(acetylacetonate)$_3$, MAO and cyclopentadienyl dimethylsilyl titanium dichlorlide In this example, 0.025 g of (p-methoxyphenyl)$_2$PN(isopropyl)P(methoxyphenyl)$_2$ [0.06 mmol] was added to 10 ml of a toluene solution of Cr(acetylacetonate)$_3$ (0.03 mmol) in a Schlenk tube under an argon atmosphere and allowed to stir for 5 minutes until fully dissolved. At the same time, 10 ml of a cyclopentadienyl dimethylsilyl titanium dichloride (0.03 mmol, 0.009 mg) solution in toluene was added to an external reservoir along with 10 ml anhydrous toluene. The external reservoir was connected to the inlet of an HPLC pump. After this, the 300 ml Parr autoclave was charged with 60 ml anhydrous toluene as well as the previously stirred Cr(acetylacetonate)$_3$/(p-methoxyphenyl)$_2$-PN(isopropyl)P(p-methoxyphenyl)$_2$ ligand solution under inert conditions. Approximately 600 eq (on Cr) methylaluminoxane (MAO) was added to the autoclave under inert conditions. The autoclave was connected to the HPLC pump outlet and heated to 45° C., sealed and pressurised to a pressure of 5300 kpa (53 barg) with ethylene for the duration of the reaction

The invention claimed is:

1. A process for polymerising olefins to branched polyolefins comprising contacting at least one olefin with a combination of catalysts comprising
   (a) a polymerisation catalyst; and
   (b) at least one co-catalyst in the form of an ethylene tetramerisation catalyst to produce 1-octene from ethylene which co-catalyst includes the combination of
      a transition metal compound; and
      a heteroatomic ligand described by the general formula

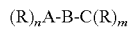

wherein
      A and C are independently an atom selected from the group consisting of phosphorus, arsenic, antimony, oxygen, bismuth, sulphur, selenium and nitrogen or said atom oxidized by S, Se, N or O where the valence of A and/or C allows for such oxidation;
      B is a linking group between A and C;
      the R groups are the same or different, and each R is independently selected from any homo or hetero hydrocarbyl group; and
      n and m for each R is independently determined by the respective valence and oxidation state of A and C; and
      provided that when the heteroatomic ligand is described by the following general formula $(R^1)(R^2)A$-$B$-$C(R^3)(R^4)$ wherein
      A and C are independently selected from the group consisting of phosphorus, arsenic, antimony, bismuth and nitrogen;
      B is a linking group between A and C; and
      $R^1$, $R^2$, $R^3$ and $R^4$ are independently selected from the group consisting of a hydrocarbyl group, a heterohydrocarbyl group, a substituted hydrocarbyl group and a substituted heterohydrocarbyl group; then $R^1$, $R^2$, $R^3$ and $R^4$ are defined by either:
      (i) no one or more of $R^1$, $R^2$, $R^3$ and $R^4$ have a substituent that is polar; and where $R^1$, $R^2$, $R^3$ and $R^4$ are independently aromatic, including heteroaromatic groups, not all the groups $R^1$, $R^2$, $R^3$ and $R^4$ have a substituent on the atom adjacent to the atom bound to A or C; or
      (ii) at least one of $R^1$, $R^2$, $R^3$ and $R^4$ has a polar substituent on a second or further atom from the atom bound to A or C and provided that none of $R^1$, $R^2$, $R^3$ and $R^4$ has any polar substituent on the atom adjacent to the atom bound to A or C.

2. The process as claimed in claim 1, wherein the olefin is ethylene and the branched polyolefin is a branched polyethylene.

3. The process as claimed in claim 1 or claim 2, wherein the branched polyolefin is linear low density polyethylene.

4. The process as claimed in claim 1, wherein the heteroatomic ligand of the co-catalyst is described by the general formula $(R^1)(R^2)A$-$B$-$C(R^3)(R^4)$ where A and C are independently selected from the group consisting of phosphorus, arsepic, antimony, bismuth, and nitrogen; B is a linking group between A and C; and $R^1$ to $R^4$ are independently selected from the group consisting of a hydrocarbyl group, a heterohydrocarbyl group, and a substituted heterohydrocarbyl group, $R^1$ to $R^4$ being defined by either:
   (i) no one or more of $R^1$, $R^2$, $R^3$ and $R^4$ have a substituent that is polar; and where $R^1$, $R^2$, $R^3$ and $R^4$ are independently aromatic, including heteroaromatic groups, not all the groups $R^1$, $R^2$, $R^3$ and $R^4$ have a substituent on the atom adjacent to the atom bound to A or C; or
   (ii) at least one of $R^1$, $R^2$, $R^3$ and $R^4$ has a polar substituent on a second or further atom from the atom bound to A or C and provided that none of $R^1$, $R^2$, $R^3$ and $R^4$ has any polar substituent on the atom adjacent to the atom bound to A or C.

5. The process as claimed in claim 4, wherein $R^1$, $R^2$, $R^3$ and $R^4$ are independently selected from the group consisting of a non-aromatic group, and an aromatic group, including a heteroaromatic group.

6. The process as claimed in claim 5, wherein each of $R^1$, $R^2$, $R^3$ and $R^4$ is independently an aromatic group, including a heteroaromatic group and not all the groups $R^1$, $R^2$, $R^3$ and $R^4$ have a substituent on the atom adjacent to the atom bound to A or C.

7. The process as claimed in claim 6, wherein not more than two of $R^1$, $R^2$, $R^3$ and $R^4$ have substituents on the atom adjacent to the atom bound to A or C.

8. The process as claimed in claim 4, wherein any polar substituent that one or more of $R^1$, $R^2$, $R^3$ and $R^4$ have is electron-donating.

9. The process as claimed in claim 1, wherein B is selected from the group consisting of an organic linking group comprising a hydrocarbylene, a substituted hydrocarbylene, a heterohydrocarbylene or a substituted heterohydrocarbylene; an inorganic linking group comprising a single atom linking spacer; and a group comprising methylene, dimethylmethylene, 1,2-ethylene, 1,2-phenylene, 1,2-propylene, 1,2-catecholate, —(CH$_3$)N—N(CH$_3$)—, —B(R$^5$)—, —Si(R$^5$)$_2$-, —P(R$^5$)—, or —N(R$^5$)—, where R$^5$ is selected from the group consisting of hydrogen, a hydrocarbyl or substituted hydrocarbyl, a substituted heteroatom, a halogen, a cyclic heteroatomic group and a cyclic homoatomic group.

10. The process as claimed in claim 9, wherein B is a single atom linking spacer.

11. The process as claimed in claim 9, wherein B is —N(R$^5$)—, wherein R$^5$ is hydrogen or selected from the group consisting of alkyl, aryl, aryloxy, halogen, alkoxycarbonyl, carbonyloxy, alkoxy, aminocarbonyl, carbonylamino, dialkylamino, or derivatives thereof, aryl substituted with any of these substituents, and any cyclic heteroatomic group including cyclopentadienyl dimethylsilyl-t-butylamidato or a cyclic homoatomic group including cyclopentadienyl, indenyl and fluorene.

12. The process as claimed in claim 1, wherein at least one or both of A and/or C is independently oxidised by S, Se, N or O, where the valence of A and/or C allows for such oxidation.

13. The process as claimed in claim 1, wherein at least one or both of A and/or C is independently phosphorus.

14. The process as claimed in claim 4, wherein $R^1$, $R^2$, $R^3$ and $R^4$ are independently selected from a group consisting of a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and a tetrahydrofuranyl group.

15. The process as claimed in claim 4, wherein $R^1$, $R^2$, $R^3$ and $R^4$ are independently selected from the group consisting of a phenyl, tolyl, biphenyl, naphthyl, thiophenenyl and ethyl group.

16. The process as claimed in claim 1, wherein the heteroatomic ligand is selected from the group consisting of (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-$^t$butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (((phenyl)$_2$)$_2$NCH$_2$CH$_2$)$_3$N, (ethyl)$_2$PN(methyl)P(ethyl)$_2$, (ethyl)$_2$PN(isopropyl)P(phenyl)$_2$, (ethyl)(phenyl)PN(methyl)P(ethyl)(phenyl), (ethyl)(phenyl)PN(isopropyl)P(phenyl)$_2$, (phenyl)$_2$P(=Se)N(isopropyl)P(phenyl)$_2$, (phenyl)$_2$PCH$_2$CH$_2$P(phenyl)$_2$, (o-ethylphenyl)(phenyl)PN(isopropyl)P(phenyl)$_2$, (o-methylphenyl)2PN(isopropyl)P(o-methylphenyl)(phenyl), (phenyl)$_2$PN(benzyl)-P(phenyl)$_2$, (phenyl)$_2$PN(1-cyclohexylethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, (phenyl)$_2$PN(2-methylcyclohexyl)P(phenyl)$_2$, (phenyl)$_2$PN(allyl)P(phenyl)$_2$, (o-naphthyl)$_2$PN(methyl)P(o-naphthyl)$_2$, (p-biphenyl)$_2$PN(methyl)P(p-biphenyl)$_2$, (p-Me-phenyl)$_2$PN(methyl)P(p-Me-phenyl)$_2$, (o-thiophenenyl)$_2$PN(methyl)P(o-thiophenenyl)$_2$, (phenyl)$_2$PN(methyl)N(methyl)P(phenyl)$_2$, (m-Me-phenyl)$_2$PN(methyl)P(m-Me-phenyl)$_2$, (phenyl)$_2$PN(isopropyl)P(phenyl)$_2$, (phenyl)$_2$P(=S)N(isopropyl)P(phenyl)$_2$, and (phenyl)$_2$P(=S)N(isopropyl)P(=S)(phenyl)$_2$.

17. The process as claimed in claim 1, wherein the heteroatomic ligand is selected from the group consisting of ((m-methoxyphenyl)$_2$PN(methyl)P(m-methoxyphenyl)$_2$, (p-methoxyphenyl)$_2$PN(methyl)P(p-methoxyphenyl)$_2$, (m-methoxyphenyl)$_2$PN(isopropyl)P(m-methoxyphenyl)$_2$, (p-methoxyphenyl)$_2$PN(isopropyl)P(p-methoxyphenyl)$_2$, (p-methoxyphenyl)$_2$PN(2-ethylhexyl)P(p-methoxyphenyl)$_2$, (m-methoxyphenyl)(phenyl)PN(methyl)P(phenyl)$_2$, (p-methoxyphenyl)(phenyl)PN(methyl)P(phenyl)$_2$, (m-methoxyphenyl)(phenyl)PN(methyl)P(m-methoxyphenyl)(phenyl), (p-methoxyphenyl)(phenyl)PN(methyl)P(p-methoxyphenyl)(phenyl), (in-methoxyphenyl)$_2$PN(methyl)P(phenyl)$_2$ and (p-methoxyphenyl)$_2$PN(methyl)P(phenyl)$_2$, (p-methoxyphenyl)$_2$PN(1-cyclohexylethyl)P(p-methoxyphenyl)$_2$, (p-methoxyphenyl)$_2$PN(2-methylcyclohexyl)P(p-methoxyphenyl)$_2$, (p-methoxyphenyl)$_2$PN(decyl)P(p-methoxyphenyl)$_2$, (p-methoxyphenyl)$_2$PN(pentyl)P(p-methoxyphenyl)$_2$, (p-methoxyphenyl)$_2$PN(benzyl)P(p-methoxyphenyl)$_2$, (p-methoxyphenyl)$_2$PN(phenyl)P(p-methoxyphenyl)$_2$, (p-fluorophenyl)$_2$PN(methyl)P(p-fluorophenyl)$_2$, (p-dimethylamino-phenyl)$_2$PN(methyl)P(p-d imethylamino-phenyl)$_2$, (p-methoxyphenyl)$_2$PN(allyl)P(p-methoxyphenyl)$_2$, (p-(p-methoxyphenyl)-phenyl)$_2$PN(isopropyl)P(p-(p-methoxyphenyl)-phenyl)$_2$ and (p-methoxyphenyl)(phenyl)PN(isopropyl)P(phenyl)$_2$.

18. The process as claimed in claim 1, wherein the polymerisation catalyst is selected from the group consisting of a Ziegler-Natta catalyst, an unbridged metallocene, a half sandwich metallocene, a carbon-bridged metallocene and a silyl-bridged metallocene.

19. The process as claimed in claim 18, wherein the Ziegler-Natta catalyst is selected from the group consisting of TiCl$_3$-Et$_2$AlCl and AlR$_3$-TiCl$_4$.

20. The process as claimed in claim 18, wherein the unbridged metallocene is selected from the group consisting of:
bis(cyclopentadienyl)chromium(II),
bis(cyclopentadienyl)-zirconium Chloride hydride,
bis(cyclopentad ienyl)-titanium dichloride,
bis(cyclopentadienyl)-zirconium dichloride,
bis(cyclopentad ienyl)-zirconium dimethyl,
bis(n-butylcyclopentadienyl)-zirconium dichloride,
bis(n-dodecylcyclopentadienyl)-zirconium dichloride,
bis(ethylcyclopentadienyl)-zirconium dichloride,
bis(iso-butylcyclopentadienyl)-zirconium dichloride,
bis(isopropylcyclopentadienyl)-zirconium dichloride,
bis(methylcyclopentadienyl)-zirconium dichloride,
bis(n-octylcyclopentadienyl)-zirconium dichloride,
bis(n-pentylcyclopentadienyl)-zirconium dichloride,
bis(n-propylcyclopentadienyl)-zirconium dichloride,
bis(trimethylsilylcyclopentadienyl)-zirconium dichloride,
bis(1,3-bis(trimethylsilyl)cyclopentadienyl)-zirconium dichloride,
bis(1-ethyl-3-methylcyclopentadienyl)-zirconium dichloride,
bis(pentamethylcyclopentadienyl)-zirconium dichloride,
bis(pentamethylcyclopentadienyl)-zirconium dimethyl,
bis(1-propyl-3-methylcyclopentadienyl)-zirconium dichloride,
bis(4,7-dimethylindenyl)-zirconium dichloride,
bis(indenyl)-zirconium dichloride,
bis(2-methylindenyl)-zirconium dichloride,
bis(2-methylindenyl)-zirconium dichloride, and
cyclopentadienylindenyl-zirconium dichloride.

21. The process as claimed in claim 18, wherein the half sandwich metallocene is selected from the group consisting of:
cyclopentadienyl-zirconium trichloride,
pentamethylcyclopentadienyl titanium trichloride,
pentamethylcyclopentadienyl-titaniumTrimethoxide,
pentamethylcyclopentadienyl-titanium Trimethyl,
pentamethylcyclopentadienyl-zirconium trichloride,
tetramethylcyclopentadienyl-zirconium trichloride, and
1,2,4-trimethylcyclopentadienyl-zirconium trichloride.

22. The process as claimed in claim 18, wherein the carbon-bridged metallocene is selected from the group consisting of:
diphenylmethylidene(cyclopentadienyl)-(9-fluorenyl)-zirconium dichloride,
diphenylmethylidene(cyclopentadienyl)-(indenyl)-zirconium dichloride,
iso-propylidenebis(cyclopentadienyl)-zirconium dichloride,
iso-propylidene(cyclopentadienyl)(9-fluorenyl)-zirconium dichloride, and
iso-propylidene(3-methylcyclopentadienyl)-(9-fluorenyl)-zirconium dichloride,
ethylene-bis(9-fluorenyl)-zirconium dichloride,
meso-ethylene-bis(1-indenyl)-zirconium dichloride,
rac-ethylene-bis(1-indenyl)-zirconium dichloride,
rac-ethylene-bis(1-indenyl)-zirconium dimethyl,
rac-ethylene-bis(2-methyl-1-indenyl)-zirconium dichloride, and
rac-ethylene-bis(4,5,6,7-tetrahydro-1-indenyl)-zirconium dichloride.

23. The process as claimed in claim 18, wherein the silyl-bridged metallocene is selected from the group consisting of:
dimethylsilyl-bis(cyclopentadienyl)-zirconium dichloride,
dimethylsilyl-bis(9-fluorenyl)-zirconium dichloride,
rac-dimethylsilyl-bis(1-indenyl)-zirconium dichloride,
meso-dimethylsilyl-bis(2-methylindenyl)-zirconium dichloride,
rac-dimethylsilyl-bis(2-methylindenyl)-zirconium dichloride,
rac-dimethylsilyl-bis(tetrahydroindenyl)-zirconium dichloride,
dimethylsilyl-bis(tetramethylcyclopentadienyl)-zirconium dichloride,
diphenylsilyl(cyclopentadienyl)(9-fluorenyl)-zirconium dichloride, and
diphenylsilyl-bis(indenyl)hafnium dichloride.

24. The process as claimed in claim 1, wherein branched polymers in the form of polyolefins are formed by means of a tandem tetramerisation due to the co-catalyst and a polymerisation process due to the polymerisation catalyst.

25. The process as claimed in claim 24, wherein the tandem tetramerisation and polymerisation process is an in-situ concurrent catalysis process and wherein tetramerisation and polymerisation takes place in the same reaction medium.

26. The process as claimed in claim 24, wherein the tandem tetramerisation and polymerisation process is an in situ consecutive catalysis process and wherein tetramerisation and polymerisation takes place in the same reaction medium.

27. The process as claimed in claim 24, wherein the tandem tetramerisation and polymerisation process is an in situ catalysis process, wherein the olefin in the form of ethylene is tetramerised using the co-catalyst to produce 1-octene and the 1-octene is copolymerized in situ with ethylene using the polymerisation catalyst and wherein tetramerisation and polymerisation takes place in the same reaction medium.

28. The process as claimed in claim 27, wherein the polymerisation catalyst includes a transition metal.

29. The process as claimed in claim 1, which includes the step of combining the heteroatomic ligand with the transition metal compound and an activator in the presence of the polymerisation catalyst.

30. The process as claimed in claim 29, wherein the transition meal of the transition metal compound is selected from the group consisting of chromium, molybdenum, tungsten, titanium, tantalum, vanadium and zirconium.

31. The process as claimed in claim 30, wherein the transition metal of the transition metal compound is chromium.

32. The process as claimed claim 1, wherein the transition metal compound of the co-catalyst is selected from the group consisting of an inorganic salt, an organic salt, a coordination complex and organometallic complex.

33. The process as claimed in claim 32, wherein the transition metal compound is selected from the group consisting of chromium trichloride tris-tetrahydrofuran complex, (benzene)-tricarbonyl chromium, chromium (III) octanoate, chromium (III) acetylacetonate, chromium hexacarbonyl and chromium (III) 2-ethylhexanoate.

34. The process as claimed in claim 33, wherein the transition metal compound is selected from the group consisting of chromium (III) acetylacetonate and chromium (III) 2-ethylhexanoate.

35. The process as claimed in claim 1, wherein the transition metal of the transition metal compound and the heteroatomic ligand are combined to provide a transition metal/ligand molar ratio from about 0.01:100 to 10 000:1.

36. The process as claimed in claim 1, wherein the co-catalyst includes an activator selected from the group consisting of an organoaluminium compound, an organoboron compound, an organic salt, an inorganic acid and an inorganic salt.

37. The process as claimed in claim 36, wherein the activator is an alkylaluminoxane.

38. The process as claimed in claim 37, wherein the transition metal compound of the co-catalyst and the aluminoxane are combined in a proportion to provide an Al/transition metal molar ratio from about 1:1 to 10 000:1.

39. The process as claimed in claim 1, wherein the heteroatomic ligand and the transition metal compound of the co-catalyst are combined at any temperature between −20° C. and 250° C. in the presence of the olefin.

40. The process as claimed in claim 1, wherein the co-catalyst and polymerisation catalyst are combined in the molar ratio of 0.01:100 to 10000:1.

41. The process as claimed in claim 1, which is carried out in an inert solvent.

42. The process as claimed in claim 1, wherein the olefin is ethylene which is contacted with the combination of catalysts at a pressure of more than 100 kPa (1 barg).

43. The process as claimed in claim 1, wherein the polymerisation catalyst and the co-catalyst are mixed at any temperature between −20° C. and 250° C. in the presence of the olefin.

44. The process as claimed in claim 1, where the process is carried out in a combination of reactors, the first reactor being a continuous stirred tank reactor and the second reactor being selected from the group consisting of a batch reactor, a continuous stirred tank reactor and a plug flow reactor.

45. A catalyst combination comprising
(a) a polymerisation catalyst; and
(b) at least one co-catalyst in the form of an ethylene tetramerisation catalyst to produce 1-octene from ethylene which co-catalyst includes the combination of
a transition metal compound; and
a heteroatomic ligand described by the general formula $(R)_nA\text{-}B\text{-}C(R)_m$ wherein
A and C are independently selected from the group consisting of phosphorus, arsenic, antimony, oxygen, bismuth, sulphur, selenium and nitrogen;
B is a linking group between A and C;
the R groups are the same or different, and each R is independently selected from any homo or hetero hydrocarbyl group; and
n and m for each R is independently determined by the respective valence and oxidation state of A and C; and
provided that when the heteroatomic ligand is described by the following general formula $(R^1)(R^2)A\text{-}B\text{-}C(R^3)(R^4)$ wherein
A and C are independently selected from the group consisting of phosphorus, arsenic, antimony, bismuth and nitrogen;
B is a linking group between A and C; and $R^1$, $R^2$, $R^3$ and $R^4$ are independently selected from the group consisting of a hydrocarbyl group, a heterohydrocarbyl group, a substituted hydrocarbyl group and a substituted heterohydrocarbyl group; then $R^1$, $R^2$, $R^3$ and $R^4$ are defined by either:

(i) no one or more of $R^1$, $R^2$, $R^3$ and $R^4$ have a substituent that is polar; and where $R^1$, $R^2$, $R^3$ and $R^4$ are independently aromatic, including heteroaromatic groups, not all the groups $R^1$, $R^2$, $R^3$ and $R^4$ have a substituent on the atom adjacent to the atom bound to A or C; or (ii) at least one of $R^1$, $R^2$, $R^3$ and $R^4$ has a polar substituent on a second or further atom from the atom bound to A or C and provided that none of $R^1$, $R^2$, $R^3$ and $R^4$ has any polar substituent on the atom adjacent to the atom bound to A or C.

* * * * *

UNITED STATES PATENT AND TRADEMARK OFFICE
CERTIFICATE OF CORRECTION

PATENT NO. : 7,323,524 B2
APPLICATION NO. : 10/538088
DATED : January 29, 2008
INVENTOR(S) : Kevin Blann et al.

It is certified that error appears in the above-identified patent and that said Letters Patent is hereby corrected as shown below:

Claim 4, col. 16, line 5,
"arsepic" should read -- aresenic --.

Claim 16, col. 17, line 23,
"(pheny)$_2$, (o-methylphenyl)2PN(isopropyl)P(o-methylphe-" should read
-- (pheny)$_2$, (o-methylphenyl)$_2$PN(isopropyl)P(o-methylphe- --.

Claim 17, col. 17, line 48,
"(p-methoxyphenyl(phenyl), (in-methoxypheynyl)$_2$PN" should read
-- (p-methoxyphenyl(phenyl), (m-methoxypheynyl)$_2$PN --

Claim 17, col. 17, line 58,
"ethylamino-phenyl)$_2$PN(methyl)P(p-d imethylamino-phe-" should read
-- ethylamino-phenyl)$_2$PN(methyl)P(p-dimethylamino-phe- --.

Claim 18, col. 18, line 9,
"bis(cyclopentad ienyl)-titanium dichloride" should read
-- bis(cyclopentadienyl)-titanium dichloride --.

Claim 18, col. 18, line 11,
"bis(cyclopentad ienyl)-zirconium dichloride" should read
-- bis(cyloclopentadienyl)-zirconium dichloride --.

Signed and Sealed this

Second Day of September, 2008

JON W. DUDAS
*Director of the United States Patent and Trademark Office*